US008918289B2

(12) United States Patent
Watanabe et al.

(10) Patent No.: US 8,918,289 B2
(45) Date of Patent: Dec. 23, 2014

(54) COMBUSTIBLE GAS DETECTION APPARATUS AND COMBUSTIBLE GAS SENSOR CONTROL METHOD

(75) Inventors: Masaya Watanabe, Komaki (JP); Ryuji Inoue, Tajimi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 422 days.

(21) Appl. No.: 13/086,810

(22) Filed: Apr. 14, 2011

(65) Prior Publication Data

US 2011/0257897 A1 Oct. 20, 2011

(30) Foreign Application Priority Data

Apr. 15, 2010 (JP) ................................ 2010-093976
Feb. 22, 2011 (JP) ................................ 2011-036033

(51) Int. Cl.
*G01N 31/00* (2006.01)
*G01N 7/00* (2006.01)
*G01N 27/12* (2006.01)

(52) U.S. Cl.
CPC .................................. *G01N 27/128* (2013.01)
USPC .......................................... 702/23; 73/23.21

(58) Field of Classification Search
USPC .................................. 702/23; 73/23.21, 23.2
See application file for complete search history.

(56) References Cited

U.S. PATENT DOCUMENTS

2004/0222094 A1* 11/2004 Ieda et al. .................... 204/424
2005/0155405 A1 7/2005 Sasaki et al.
2007/0110618 A1* 5/2007 Sasanuma et al. ........... 422/68.1
2008/0116071 A1* 5/2008 Nakamura et al. ............ 204/427
2010/0084287 A1* 4/2010 Teramoto et al. ............ 205/785

FOREIGN PATENT DOCUMENTS

JP 6-11472 A 1/1994
JP 2004-251862 A 9/2004
JP 2005-156364 A 6/2005
JP 2007-309751 A 11/2007
JP 2008-267948 A 11/2008

OTHER PUBLICATIONS

Office Action issued on Feb. 6, 2014 for corresponding Japanese Patent Application No. 2011-036033.
Office Action issued on Dec. 2, 2013 for corresponding Japanese Patent Application No. 2011-036033.

* cited by examiner

*Primary Examiner* — Sujoy Kundu
*Assistant Examiner* — Ricky Ngon
(74) *Attorney, Agent, or Firm* — Sughrue Mion, PLLC

(57) ABSTRACT

There is provided a combustible gas detection apparatus with a gas sensor and a control device. The gas sensor includes first and second heating resistors each having a resistance that changes depending on a combustible gas concentration of gas under measurement. The control device includes an energization control section that alternately energizes the first and second heating resistors, a first calculation section that calculates a first calculation value responsive to the combustible gas concentration based on a voltage across the first heating resistor during energization of the first heating resistor, a second calculation section that calculates a second calculation value responsive to the combustible gas concentration based on a voltage across the second heating resistor during energization of the second heating resistor, and an anomaly judgment section that judges the occurrence of an anomaly in the first heating resistor by comparison of the first and second calculation values.

14 Claims, 10 Drawing Sheets

COMBUSTIBLE GAS DETECTION APPARATUS AND COMBUSTIBLE GAS SENSOR CONTROL METHOD

BACKGROUND OF THE INVENTION

The present invention relates to a combustible gas detection apparatus equipped with a combustible gas sensor to measure the concentration of a combustible gas component in a gas under measurement. The present invention also relates to a control method of a combustible gas sensor.

In recent years, intensive researches have been made on fuel cells as high-efficiency, clean energy sources in accordance with the social demands for environmental protection and nature conservation. Among others, polymer electrolyte fuel cells (PEFC) and hydrogen internal combustion engines are expected to be useful as energy sources for home and automotive applications because of their advantageous performance such as low temperature operability and high output density. As each of these fuel cell systems utilizes a combustible hydrogen gas as a fuel, the detection of a gas leak from the fuel cell system is one important problem to overcome. It is thus common practice to use, in the fuel cell system, a combustible gas detection apparatus for measuring the concentration of a combustible gas component in a gas under measurement.

There is known a conventional type of combustible gas detection apparatus, which includes a heating resistor placed in a gas under measurement and having a resistance that changes depending on a combustible gas concentration of the gas under measurement and a bridge circuit adapted to control the resistance of the heating resistor to a given level corresponding to a predetermined setting temperature and output a voltage across the heating resistor under such resistance control (referred to as "resistor control voltage") as a detection value responsive to the combustible gas concentration.

In the above conventional type of combustible gas detection apparatus, however, the relationship of the gas concentration and the resistor control voltage varies with the resistance and heat capacity of the heating resistor during long-term use. This can result in an error in the gas concentration detection value (see FIG. 5A).

In view of such a problem, Japanese Laid-Open Patent Publication No. 2004-251862 discloses a combustible gas detection apparatus, which includes two adjacent heating resistors: one heating resistor is as a reference element and the other heating resistor is as a sensor element and diagnosis means for, at the time of deterioration diagnosis of the sensor element, simultaneously operating the reference element and the sensor element and comparing a gas concentration detection value of the reference element with a gas concentration detection value of the sensor element.

SUMMARY OF THE INVENTION

In the case of using two heating resistors in the combustible gas detection apparatus as disclosed in Japanese Laid-Open Patent Publication No. 2004-251862, the output matching (the adjustment of the relationship of the gas concentration and the resistor control voltage) is done separately for each of the two heating resistors during manufacturing. Further, the two heating resistors are generally mounted on the same substrate as it is necessary to locate the two heating resistors as close as possible so that these heating resistors perform gas concentration detection operations in the same area. The combustible gas detection apparatus of Japanese Laid-Open Patent Publication No. 2004-251862 thus faces a problem of deterioration in anomaly detection accuracy when the output characteristics of the reference element vary under the influence of heat generated from the sensor element.

It is accordingly an object of the present invention to solve the above-mentioned prior art problems and provide a combustible gas detection apparatus that includes a plurality of heating resistors, one of which is as a sensor element, and attains the improved accuracy of detection of an anomaly in the sensor element.

According to one aspect of the present invention, there is provided a combustible gas detection apparatus for measuring a combustible gas concentration of a gas under measurement, comprising: a combustible gas sensor having first and second heating resistors, each of which being placed in the gas under measurement and having a resistance that changes depending on the combustible gas concentration of the gas under measurement; and a control device having: an energization control section that alternately energizes the first and second heating resistors in such a manner as to adjust the resistance of each of the first and second heating resistors to a given value corresponding to a predetermined setting temperature; a first calculation section that calculates a first calculation value responsive to the combustible gas concentration of the gas under measurement based on a voltage across the first heating resistor during energization of the first heating resistor; a second calculation section that calculates a second calculation value responsive to the combustible gas concentration of the gas under measurement based on a voltage across the second heating resistor during energization of the second heating resistor; and an anomaly judgment section that judges the occurrence or non-occurrence of an anomaly in the first heating resistor by comparison of the first and second calculation values.

As mentioned above, the combustible gas detection apparatus is configured to alternately energize the first and second heating resistors. In other words, the combustible gas detection apparatus causes de-energization of the second heating resistor during energization of the first heating resistor for calculation of the first calculation value, so as to prevent heat generation of the second heating resistor and obtain the first calculation value as the output of the first heating resistor without the influence of heat generated by the second heating resistor. On the other hand, the combustible gas detection apparatus causes de-energization of the first heating resistor during energization of the second heating resistor for calculation of the second calculation value, so as to prevent heat generation of the first heating resistor and obtain the second calculation value as the output of the second heating resistor without the influence of heat generated by the first heating resistor. It is therefore possible for the combustible gas detection apparatus to detect the anomaly in the first heating resistor accurately by comparison of these first and second calculation values.

It is further preferable that the first and second heating resistors are preferably mounted on the same substrate as these first and second heating resistors need to be located as close as possible to each other to preform gas concentration detection operations in the same atmosphere of the gas under measurement. This leads to not only improvement of the anomaly detection accuracy of the combustible gas detection accuracy but also size reduction of the combustible gas detection apparatus and simplification of mounting/assembling of the heating resistors during manufacturing of the combustible gas detection apparatus.

In general, it is difficult to mount two heating resistors on the same substrate due to the fact that, when two heating resistors are mounted on the same substrate, one of the heating resistors becomes affected under the influence of heat generated by the other heating resistor. In the present invention, however, the first and second heating resistors can be mounted on the same substrate, without becoming thermally affected by each other, by alternate energization control of the first and second heating resistors.

The alternate energization control of the present invention is particularly effective when the gas sensor is produced by micromachining a silicon substrate and arranging the first and second heating resistors in an insulating film on the silicon substrate. The above-produced gas sensor is so small in size that the first and second heating resistors are located very close to each other in the insulating film and readily allow heat transfer therebetween through the insulating film. This makes it more likely that one of the heating resistors will become affected under the influence of heat generated by the other heating resistor. Even in such a case, it is possible by the alternate energization control of the first and second heating resistors to obtain the first and second calculation values, without the first and second heating resistors being thermally affected by each other, and thereby possible to detect the anomaly in the first heating resistor accurately by comparison of the first and second calculation values.

It is also preferable that the anomaly judgment section is actuated every time a predetermined judgment condition is satisfied for assured and accurate detection of the anomaly in the first heating resistor. As the predetermined judgment condition, there can be set the lapse of a predetermined time or the activation of equipment such as a vehicle in which the combustible gas detection apparatus is installed.

Furthermore, the sensor control device preferably has a normal-state operation section that, upon satisfaction of the predetermined judgment condition, causes the energization control section to allow the energization of the second heating resistor only during a time period required to measure the voltage across the second heating resistor for calculation of the second calculation value and allow the energization of the first heating resistor at all times other than the above time period. This makes it possible to reduce the frequency of use of the second heating resistor as compared to that of the first heating resistor and prevent deterioration of the second heating resistor. The output characteristics of the second heating resistor can be thus maintained at or near the initial level over a long time for further improvement in the accuracy of detection of the anomaly in the first heating resistor.

The sensor control device also preferably has an abnormal-state operation section (occasionally referred to as "first abnormal-state operation section") that, when the anomaly judgment section judges that the anomaly is occurring in the first heating resistor, causes the energization control section to stop the energization of the first and second heating resistors. This makes it possible to cancel the gas concentration detection operations of the combustible gas detection apparatus upon detecting the occurrence of the anomaly in the first heating resistor and prevent the occurrence of detection errors due to the use of such an abnormally-functioning first heating resistor.

The sensor control device may alternatively preferably have another type of abnormal-state operation section (occasionally referred to as "second abnormal-state operation section") that, when the anomaly judgment section judges that the anomaly is occurring in the first heating resistor, causes the energization control section to energize the second heating resistor and causes the second calculation section to calculate the second calculation value. This makes it possible to continue the gas concentration detection operations of the combustible gas detection apparatus by means of the second heating resistor even after the detection of the anomaly in the first heating resistor, i.e., even in the occurrence of deterioration of the first heating resistor and thereby possible to increase the operable time (operation life) of the combustible gas detection apparatus.

It is feasible that the anomaly judgment section judges the occurrence of the anomaly in the first heating resistor when either a difference between the first and second calculation values or a ratio between the first and second calculation value exceeds a given threshold value. There is no particular limitation on the first and second calculation values as long as the first and second calculation values have a clear correlation with the combustible gas concentration. The voltages across the first and second heating resistors may be set as they are as the first and second calculation values. This leads to a significant reduction in the amount of data processing for judgment of the occurrence of the anomaly in the first heating resistor. Alternatively, the first and second calculation values may be impedances or gas concentration values converted from the voltages across the first and second heating resistors. Further, each of the first and second calculation values can be in the form of an average value (local average, moving average, weight average etc.) of the voltage across the heating resistor, or the impedance or gas concentration value converted from the voltage across the heating resistor, over a fixed time period.

It is further feasible that the energization control section has a first energization controller that controls the energization of the first heating resistor and a second energization controller that controls the energization of the second heating resistor and operate the first and second energization controllers alternately for the alternate energization control of the first and second heating resistors. Alternatively, it is feasible that the energization control section has a selector that selects either one of the first and second heating resistors as an energization control target and an energization controller (occasionally referred to as "third energization controller") that controls the energization of the selected one of the first and second heating resistors. In the latter case, the energization control section can be more simplified in configuration.

According to another aspect of the present invention, there is provided a control method of a combustible gas sensor, the gas sensor comprising a plurality of heating resistors, each of which being placed in a gas under measurement and having a resistance that changes depending on a combustible gas concentration of the gas under measurement, one of the heating resistors being used as a sensor element, another one of the heating resistor being used as a reference element; the control method comprising: energizing each of the sensor element and the reference element in such a manner as to adjust the resistance of each of the sensor element and the reference element to a given level corresponding to a predetermined setting temperature; calculating a first calculation value responsive to the combustible gas concentration of the gas under measurement based on a voltage across the sensor element during energization of the sensor element; calculating a second calculation value responsive to the combustible gas concentration of the gas under measurement based on a voltage across the reference element during energization of the reference element; and judging the occurrence or non-occurrence of an anomaly in the sensor element by comparison of the first and second calculation values, wherein the energizing is performed by de-energizing any of the heating resistors other than that used as the sensor element during the energization of the sensor element and by de-energizing any of the heating resistors other than that used as the reference element during the energization of the reference element.

It is possible by this sensor control method to obtain the first and second calculation values as the outputs of the sensor and reference resistor elements, without the influence of heat generated by any other heating resistor element, and thereby possible to detect the anomaly in the sensor element accurately by comparison of these first and second calculation values.

The other objects and features of the present invention will also become understood from the following description.

DESCRIPTION OF THE EMBODIMENTS

Figure 1:
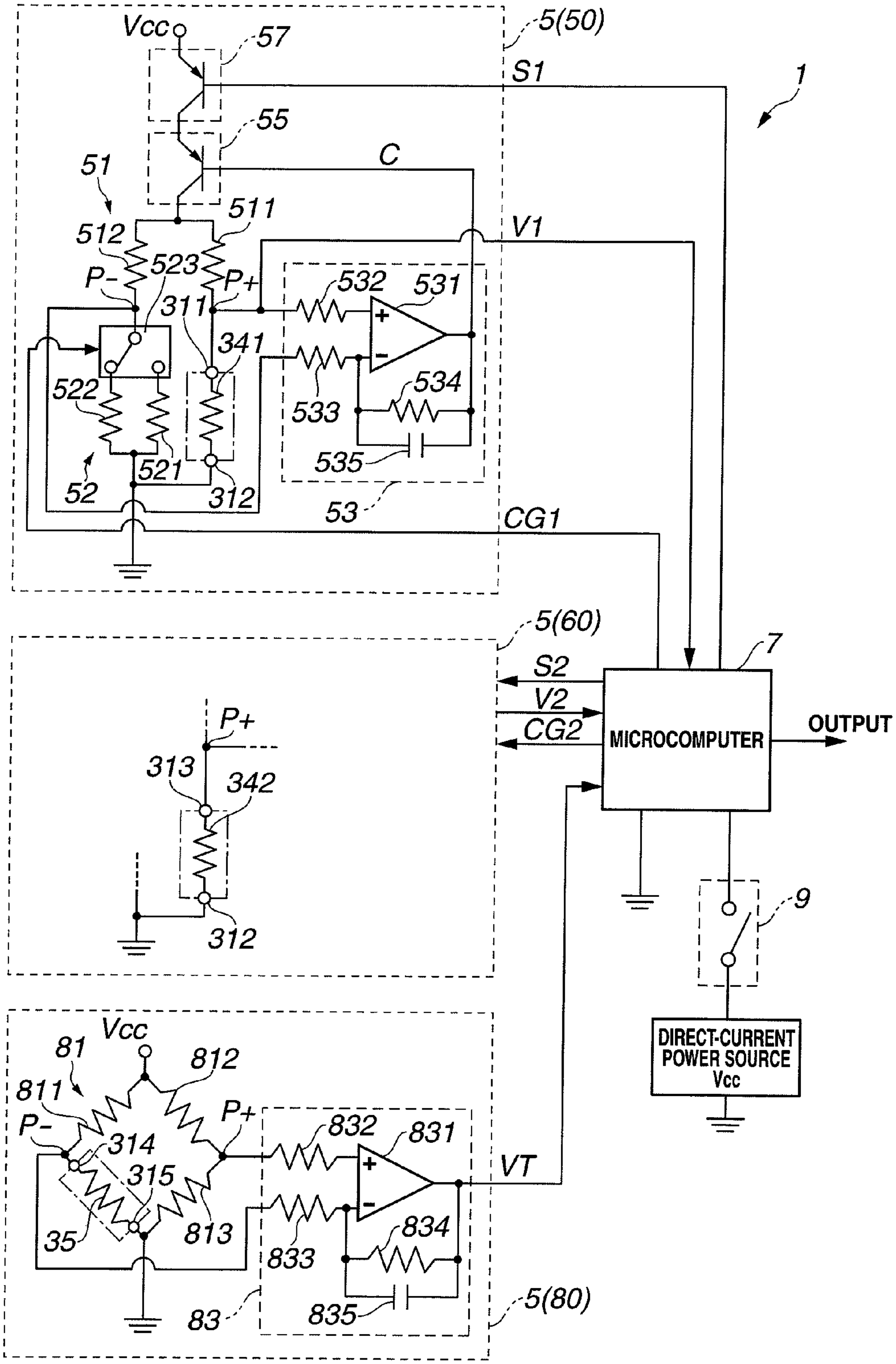
FIG. 1 is a block diagram of a combustible gas detection apparatus according to a first embodiment of the present invention.

The present invention will be described in more detail below by way of the following first to fourth embodiments, in which like parts and portions are designated by like reference numerals to avoid repeated explanations thereof. It is noted that the following first to fourth embodiments are illustrative and are not intended to limit the present invention thereto.

First Embodiment

The first embodiment specifically refers to a combustible gas detection apparatus 1 designed for use in, for example, a fuel cell vehicle to detect the occurrence of leakage of a combustible gas such as hydrogen from the fuel cell vehicle.

As shown in FIG. 1, the combustible gas detection apparatus 1 includes a thermal-conductive gas sensor 3 placed in and exposed to a gas under measurement to measure the concentration of a combustible gas component such as hydrogen in the gas under measurement, a drive control circuit assembly 5 for performing drive control of the gas sensor 3, a microcomputer 7 for generating various control signals such as energization signals S1 and S2 and switching signals CG1 and CG2 to control operations of the drive control circuit assembly 5 and performing various operation processes including gas concentration measurement process based on output signals V1, V2 and VT from the drive control circuit assembly 5, and an actuation switch 9 for connecting or disconnecting a power supply line from a direct-current power source Vcc to the microcomputer 7 and thereby actuating or stopping the microcomputer 7. In the first embodiment, the drive control circuit assembly 5, the microcomputer 7 and the actuation switch 8 are mounted on the same circuit board, which is constructed separately from the gas sensor 3, and constitute a sensor control device.

Figure 2A:
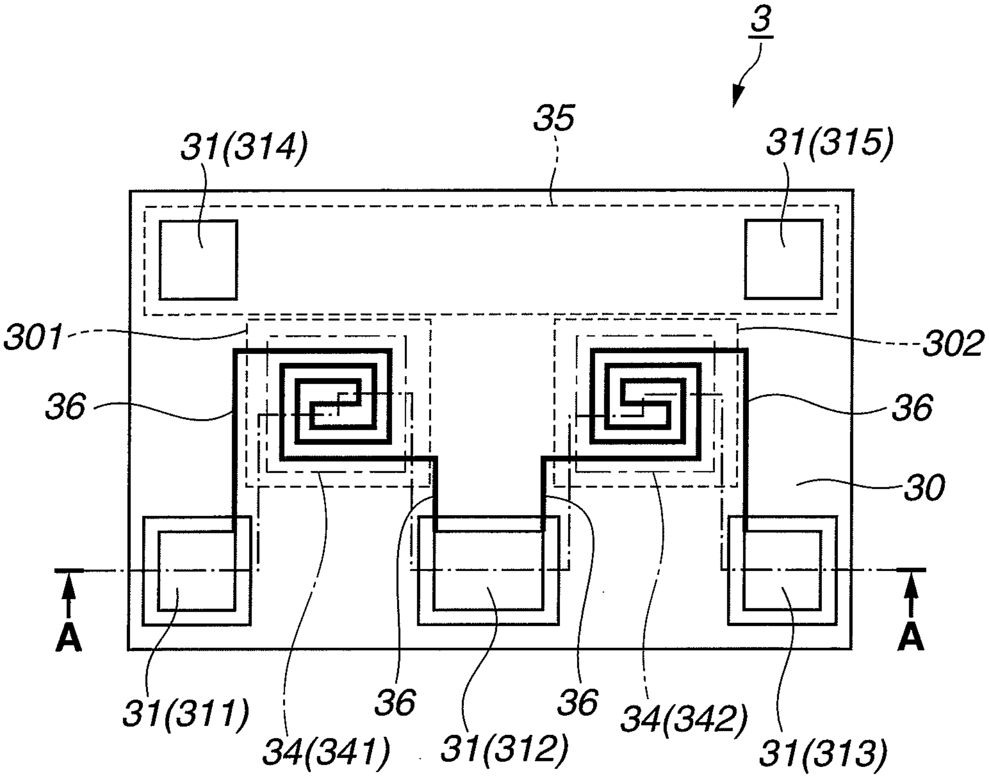
FIG. 2A is a plan view of a gas sensor as a substantial part of the combustible gas detection apparatus according to the first embodiment of the present invention.
Figure 2B:
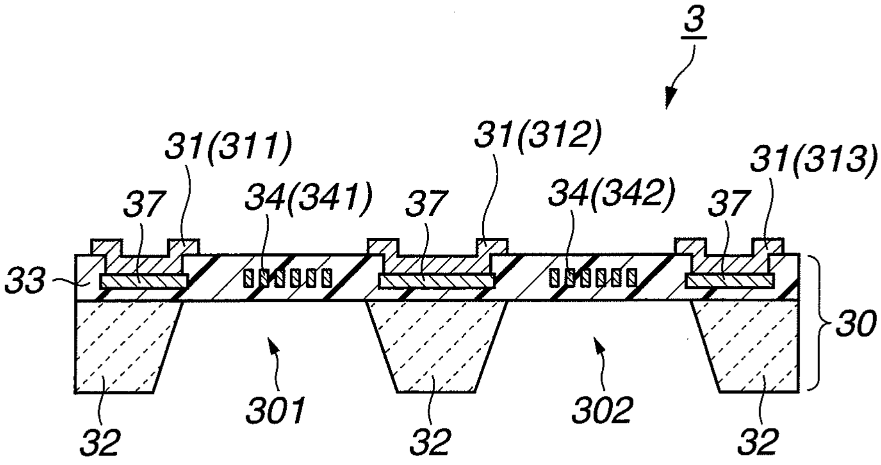
FIG. 2B is a cross section view of the gas sensor taken along line A-A of FIG. 2A.

As shown in FIGS. 2A and 2B, the gas sensor 3 has a rectangular plate-shaped sensor body 30, a plurality of electrodes 31 formed in one surface (referred to as "front surface") of the sensor body 30 and two recesses 301 and 302 formed in a center portion of the other surface (referred to as "rear surface") of the sensor body 30 along a longitudinal direction of the sensor body 30. Herein, the electrodes 31 includes three electrodes 311, 312 and 313 (referred to as "first electrodes") arranged along one longitudinal side of the sensor body 30 and two electrodes 314 and 315 (referred to as "second electrodes") arranged along the other longitudinal side of the sensor body 30. The electrodes 312 and 315 are also referred to as ground electrodes. These electrodes 31 are made of e.g. aluminum (Al) or gold (Au).

The sensor body 30 includes a silicon substrate 32 and an insulating film 33 arranged on one surface of the silicon substrate 32. As shown in FIG. 2B, the sensor body 30 has a diaphragm structure in which given portions (e.g. square portions) of the silicon substrate 32 are removed to define the recesses 301 and 302 such that corresponding portions of the insulating film 33 are exposed through the recesses 301 and 302. That is, the term "front" refers to an insulating-film side of the sensor body 30; and the term "rear" refers to a silicon-substrate side of the sensor body 30.

In the first embodiment, the sensor body 30 has width and length dimensions of several mm (e.g. 3 mm×5 mm) and is produced by micromachining the silicon substrate 32. Further, the insulating film 33 can be in the form of a single material layer or a plurality of layers of different materials. As the material of the insulating film 33, there are suitably used silicon oxide ($SiO_2$), silicon nitride ($Si_3N_4$) and the like.

The sensor body 30 also has a pair of heating resistors 34 (first and second heating resistors 341 and 342) embedded in the portions of the insulating film 33 exposed through the recesses 301 and 302, respectively, and a temperature-measuring resistor 35 embedded in the longitudinal edge portion of the insulating film 33 on which the second electrodes 314 and 315 are formed. The heating resistors 34 are made of a conductive material which shows a large temperature coefficient of resistance and has an electrical resistance that changes with temperature (in the first embodiment, increases with temperature). As shown in FIG. 2A, each of the heating resistors 34 is in the form of a spiral-wound wire in the first embodiment. On the other hand, the temperature-measuring resistor 35 is made of a conductive material which has an electrical resistance that changes in proportion to temperature (in the first embodiment, increases with temperature). In the first embodiment, both of the heating resistors 34 and the temperature-measuring resistor 35 are made of the same material such as platinum (Pt).

Further, the heating resistors 34 are connected to the first electrodes 311, 312 and 313 via wiring elements 36 and wiring films 37, which are embedded in the insulating film 33 in such a manner that the heating resistors 34, the wiring elements 36 and the wiring films 37 are located in the same plane. The temperature-measuring resistor 35 is connected to the second electrodes 314 and 315 via wiring films, which are embedded in the insulating film 33 in such a manner that the temperature-measuring resistor 35 and the insulating films are located in the same plane although not so shown in the drawings. As the material of the wiring elements and films 36 and 37 for connection of the heating resistors 34 to the first electrodes 311, 312 and 313 as well as the wiring films for connection of the temperature-measuring resistor 35 to the second electrodes 314 and 315, there can be used the same resistance material as that of the resistors 34 and 35. There are also provided contact holes (as connection conductors) for connection of the electrodes 31 formed on the front surface of the sensor body 30 and the wiring films 37 formed in the sensor body 30 (insulating film 33).

Namely, the first heating resistor 341 has one end connected to the first electrode 311 and the other end connected to the ground electrode 312; the second heating resistor 342 has one end connected to the first electrode 313 and the other end connected to the ground electrode 312; and the temperature-measuring resistor 35 has one end connected to the second electrode 314 and the other end connected to the ground electrode 315 as shown in FIG. 2A. In the first embodiment, the first and second heating resistors 341 and 342 serve as a sensor element and a reference element, respectively.

As shown in FIG. 1, the drive control circuit assembly 5 includes a first energization control unit 50 to perform energization control of the first heating resistor 341 and output a voltage across the first heating resistor 341 as the detection signal V1, a second energization control unit 60 to perform energization control of the second heating resistor 342 and output a voltage across the second heating resistor 342 as the detection signal V2 and a temperature measurement unit 80 to perform energization control of the temperature-measuring resistor 35 and output the detection signal VT responsive to the temperature of the gas under measurement. In the first embodiment, the first and second energization control units 50 and 60 serve as first and second energization controllers, respectively.

The first energization control unit 50 has a bridge circuit (Wheatstone bridge circuit) 51 in which the first heating resistor 34 is incorporated, an amplifier circuit 53 to amplify a potential difference in the bridge circuit 51, a current regulator circuit 55 to regulate (increase or decrease) the flow of current through the bridge circuit 51 and a switching circuit 57 to turn on and off energization of the bridge circuit 51.

The switching circuit 57 consists of a transistor that is connected to the direct-current power source Vcc and adapted to make switching on/off operations according to the energization signal S1 from the microcomputer 7.

The current regulator circuit 55 consists of a transistor that is connected in series to the switching circuit 57 on the power supply line from the direct-current power source Vcc and so adapted that the energization state (on-resistance) of the transistor changes according to an output signal (referred to as "current regulation signal") C from the amplifier circuit 53. In the first embodiment, the on-resistance of the transistor increases with the current regulation signal C so as to decrease the flow of current through the bridge circuit 51 and decreases with the regulation signal C so as to increase the flow of current through the bridge circuit 51.

The amplifier circuit 53 has a known differential amplifier circuit configuration including an operational amplifier 531, fixed resistors 532 and 533 connected to non-inverting and inverting input terminals of the operational amplifier 531, respectively, and a fixed resistor 534 and a capacitor 535 connected in parallel between the inverting input terminal and output terminal of the operational amplifier 531, so as to output the current regulation signal C to the current regulator circuit 55. In this configuration, the amplifier circuit 53 is adapted to increase the current regulation signal C (and thereby decrease the flow of current through the bridge circuit 51) when the input voltage of the non-inverting input terminal of the operational amplifier 531 is higher than the input voltage of the inverting input terminal of the operational amplifier 531 and to decrease the current regulation signal C (and thereby increase the flow of current through the bridge circuit 51) when the input voltage of the non-inverting input terminal of the operational amplifier 531 is lower than the input voltage of the inverting input terminal of the operational amplifier 531.

The bridge circuit 51 incorporates therein the first heating resistor 341 as a bridge circuit component and also has two fixed resistors 511 and 512 and a variable resistance element 52. The resistance element 52 has a resistance switched between two resistance values. The first heating resistor 341 and the fixed resistor 511 are connected in series, whereas the fixed resistor 512 and the variable resistance element 52 are connected in series. In these series circuits, the first heating resistor 341 and the variable resistance element 52 are connected at terminals thereof to the ground; and the fixed resistors 511 and 512 are connected at terminals thereof to the power supply side (current regulator circuit 55). Further, a junction P+ of the fixed resistor 511 and the first heating resistor 341 is connected to the non-inverting input terminal of the operational amplifier 531 via the fixed resistor 532; and a junction P− of the fixed resistor 512 and the variable resistance element 52 is connected to the inverting input terminal of the operational amplifier 531 via the fixed resistor 533. The bridge circuit 51 is thus adapted to output the potential at the junction P+ (i.e. the voltage across the first heating resistor 341) as the detection signal V1 to the microcomputer 7.

In the first embodiment, the variable resistance element 52 has two fixed resistors 521 and 522 of different resistance values and a selector switch 523 to actuate either one of the fixed resistors 521 and 522 according to the switching signal S1 from the microcomputer 7 so that the balance of the bridge circuit 51 can be changed upon switching of the resistance of the variable resistor element 52 by means of the selector switch 523. The fixed resistor 521 has a resistance value corresponding to a first setting temperature CH (e.g. 300° C.) of the first heating resistor 341; whereas the fixed resistor 522 has a resistance value corresponding to a second setting temperature CL (e.g. 200° C.) of the first heating resistor 341 that is lower than the first setting temperature CH.

The above first energization control unit 50 operates as follows. When the switching circuit 57 is switched on to start energization of the bridge circuit 51 according to the energization signal S1 from the microcomputer 7, the amplifier circuit 53 and the current regulator circuit 55 are operated to regulate the flow of current through the bridge circuit 51 in such a manner that the potential difference between the junctions P+ and P− becomes zero. Under such current regulation control, the resistance of the first heating resistor 341 is adjusted to a given constant level depending on the resistance value of the fixed resistor 521 or 522 of the variable resistance element 52 whereby the temperature of the first heating resistor 341 is controlled to the first setting temperature CH or the second setting temperature CL. More specifically, the first heating resistor 341 decreases in resistance with temperature when the combustible gas concentration of the gas under measurement varies so that the amount of heat taken by the combustible gas becomes greater than the amount of heat generated by the first heating resistor 341. As the resistance of the first heating resistor 341 decreases, the amplifier circuit 53 and the current regulator circuit 55 are operated to increase the flow of current through the bridge circuit 51 and thereby increase the amount of heat generated by the first heating resistor 341 to the given level. On the other hand, when the combustible gas concentration of the gas under measurement varies so that the amount of heat taken by the combustible gas becomes smaller than the amount of heat generated by the first heating resistor 341, the first heating resistor 341 increases in resistance with temperature. As the resistance of the first heating resistor 341 increases, the amplifier circuit 53 and the current regulator circuit 55 are operated to decrease the flow of current through the bridge circuit 51 and thereby decrease the amount of heat generated by the first heating resistor 341 to the given level. The resistance (temperature) of the first heating resistor 341 is thus maintained at the given constant level.

Namely, the combustible gas concentration X can be determined from the detection signal V1 as the detection signal V1 (the potential at the junction P+) is responsive to the intensity of current through the first heating resistor 341, i.e., the amount of heat required to maintain the temperature (resistance) of the first heating resistor 341 at the given level and, by extension, the amount of heat taken by the combustible gas that varies depending on the combustible gas concentration of the gas under measurement.

The second energization control unit 60 is similar in configuration to the first energization control unit 50, except that the second energization control unit 60 incorporates therein the second heating resistor 342 in place of the first heating resistor 341, receives the energization signal S2 and the switching signal CG2 in place of the energization signal S1 and the switching signal CG1, respectively, and outputs the detection signal V2 in place of the detection signal V1. Detailed explanations of the structure and operations of the second energization control unit 60 will be thus omitted.

The temperature measurement unit 80 includes a bridge circuit (Wheatstone bridge circuit) 81 in which the temperature-measuring resistor 35 is placed and an amplifier circuit 83 to amplify a potential difference in the bridge circuit 81.

The amplifier circuit 83 has a known differential amplifier circuit configuration including an operational amplifier 831, fixed resistors 832 and 833 connected to non-inverting and inverting input terminals of the operational amplifier 831, respectively, and a fixed resistor 834 and a capacitor 835 connected in parallel between the inverting input terminal and output terminal of the operational amplifier 831.

The bridge circuit 81 incorporates therein the temperature-measuring resistor 35 as a bridge circuit component and also has three fixed resistors 811, 812 and 813. The fixed resistor 811 and the temperature-measuring resistor 35 are connected in series, whereas the fixed resistors 812 and 813 are connected in series. In these series circuits, the temperature-measuring resistor 35 and the fixed resistor 813 are connected at terminals thereof to the ground; and the fixed resistors 811 and 812 are connected at terminals thereof to the power supply side. Further, a junction P− of the fixed resistor 811 and the temperature-measuring resistor 35 is connected to the inverting input terminal of the operational amplifier 831 via the fixed resistor 833; and a junction P+ of the fixed resistors 811 and 813 is connected to the non-inverting input terminal of the operational amplifier 831 via the fixed resistor 832. The bridge circuit 81 is thus adapted to send the output of the operational amplifier 813 as the detection signal VT to the microcomputer 7. More specifically, the temperature-measuring resistor 35 is set in such a manner that the temperature detection signal VT is at a reference level when the temperature of the gas under measurement to which the gas sensor 3 is exposed is a given reference temperature. As the resistance of the temperature-measuring resistor 35 varies depending on the temperature of the gas under measurement, there arises a potential difference in the temperature-measuring resistor 35 in response to the difference between the reference temperature and the temperature of the gas under measurement. This potential difference is amplified and outputted as the detection signal VT.

For connection of the gas sensor 3 and the drive control circuit assembly 5, the first electrodes 311 and 313 are connected to the junction point P+ of the first energization control unit 50 and the junction point P+ of the second energization control unit 60, respectively; the second electrode 314 is connected to the junction point P− of the temperature measurement unit 80; and the ground electrodes 312 and 315 are connected to a common ground line of the drive control circuit assembly 5.

The microcomputer 7 has a known hardware configuration including at least a storage unit (such as a ROM, a RAM etc.) to store therein various data and programs for gas concentration measurement process, a CPU to execute any of the programs stored in the storage unit, I/O ports to output the control signals S1, S2, CG1 and CG2 to the drive control circuit assembly 5 and receive input of the detection signals V1, V2 and VT from the drive control circuit assembly 5 and a timer.

Herein, the voltage level of the detection signal Vi (i=1, 2) detected from the energization control unit 50, 60 at the first setting temperature (300° C.) is referred to as "high-temperature concentration detection voltage VHi"; the voltage level of the detection signal Vi (i=1, 2) detected from the energization control unit 50, 60 at the second setting temperature (200° C.) is referred to as "low-temperature concentration detection voltage VLi"; and the voltage level of the detection signal VT detected from the temperature measurement unit 80 is referred to as "temperature detection voltage VT".

In the first embodiment, the storage unit stores therein at least temperature conversion data indicating the correlation of the ambient temperature T of the gas under measurement with the temperature detection voltage VT, humidity conversion data indicating the correlation of the humidity H of the gas under measurement with the high-temperature concentration detection voltage VHi, low-temperature concentration detection voltage VLi and temperature detection voltage VT and concentration conversion data indicating the correlation of the combustible gas concentration X with the high-temperature concentration detection voltage VHi or low-temperature concentration detection voltage VLi. Each conversion data can be in the form of a conversion map, a calculation formula or the like and has previously been created by experiment etc. Further, the storage unit has a concentration storage area required to store therein all of calculation results of the combustible gas concentration X over the after-mentioned judgment operation period.

The above-configured combustible gas detection apparatus 1, in which the first and second heating resistors 341 and 342 serve as the sensor element and the reference element, respectively, as mentioned above, has a normal operation mode in which the first heating resistor 341 is energized for a predetermined time period to calculate a gas concentration value X1 based on the detection signal V1 of the first heating resistor 341 as the combustible gas concentration X and a judgment operation mode in which the first and second heating resistors 341 and 342 are energized for a predetermined time $\Delta T$ (referred to as "judgment time") to calculate gas concentration values X1 and X2 based on the detection signals V1 and V2 of the first and second heating resistors 341 and 342, respectively, and judge the occurrence or non-occurrence of an anomaly in the sensor element 341 by comparison of the gas concentration values X1 and X2. In the judgment operation mode, however, there is a possibility that the occurrence of the anomaly in the sensor element 341 may not be judged accurately as the detection signal V1, V2 of one of the heating resistors 341 and 342 becomes affected under the influence of heat generated by the other of the heating resistors 341 and 342.

Figure 3:
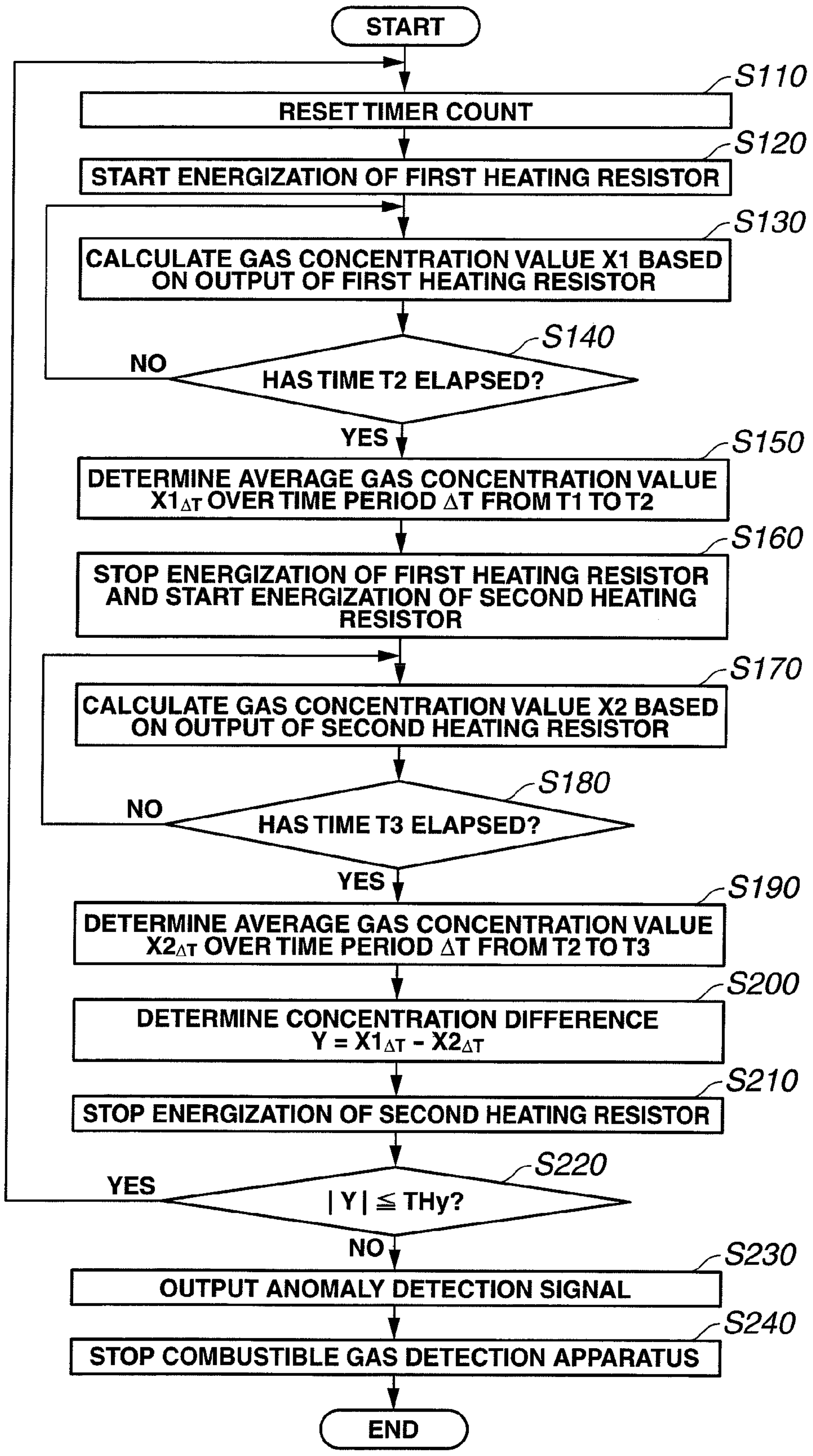
FIG. 3 is a flowchart of gas concentration measurement process of the combustible gas detection apparatus according to the first embodiment of the present invention.

In order to avoid such an anomaly detection accuracy deterioration problem, the combustible gas detection apparatus 1 executes the gas concentration measurement process through the following steps as shown in FIG. 3.

The microcomputer 7 first initializes its hardware units upon turning on the actuation switch 9 to start the power supply from the direct-current power source Vcc to the microcomputer 7.

At step S110, the microcomputer 7 first resets the timer count.

At step S120, the microcomputer 7 outputs the energization signal S1 to the first energization control unit 50 so as to start energization of the bridge circuit 51 (the first heating resistor 341) of the first energization control unit 50. At the time the energization of the first heating resistor 341 is started for the first time in the gas concentration measurement process, the second heating resistor 342 is in a de-energization state.

At step S130, the microcomputer 7 calculates the gas concentration value X1 from the detection voltages VL1 or VH1 and VT, stores the calculated gas concentration value X1 in the storage unit and outputs the calculated gas concentration value X1 to the external device.

Figure 4:
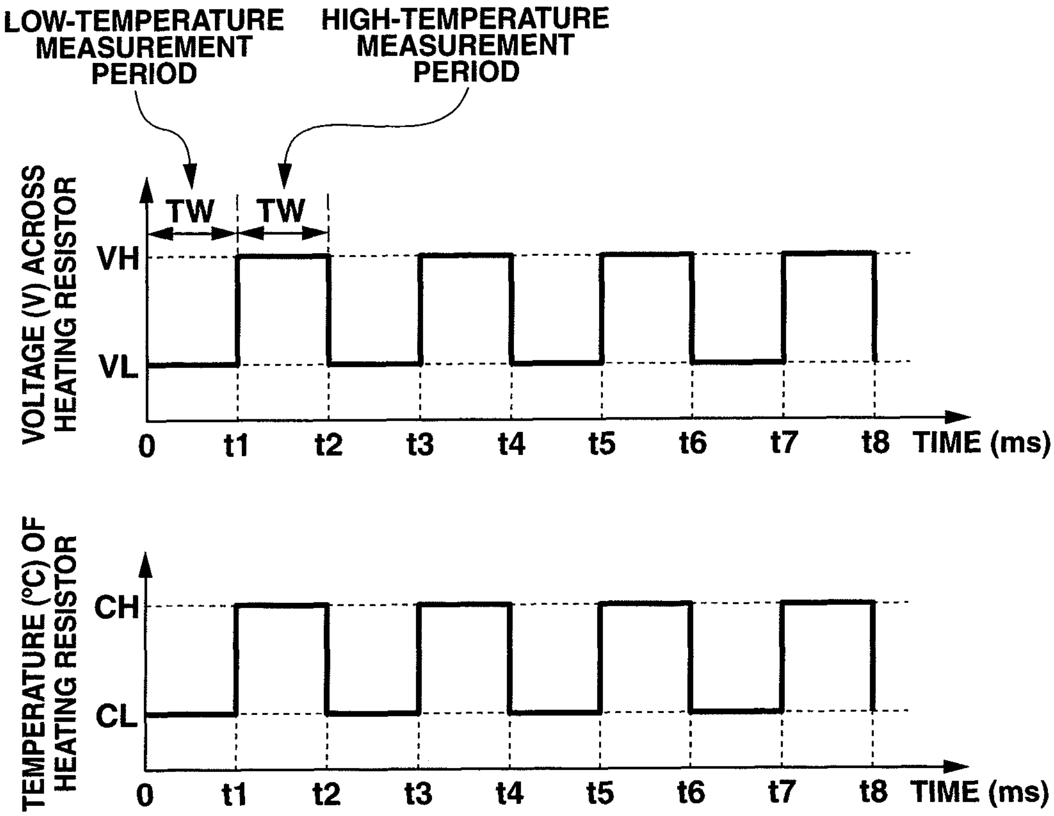
FIG. 4 is a time chart showing how to change temperature settings and determine voltage parameters for the gas sensor in the gas concentration measurement process.

More specifically, the resistance of the bridge circuit 51 is switched under the switching signal CG1 from the microcomputer 7 so as to maintain the setting temperature of the first heating resistor 341 at the second setting temperature CL in a fixed time period TW (referred to as "low-temperature measurement period"), and then, maintain the setting temperature of the first heating resistor 341 at the first setting temperature CH in a fixed time period TW (referred to as "high-temperature measurement period") as shown in FIG. 4. The fixed time period TW is herein set to be longer than or equal to a period of time sufficient to stabilize the detection signal V1 after the switching of the setting temperature of the first heating resistor 341. In general, the fixed time period is set to about several hundreds ms (e.g 200 ms).

In parallel to such temperature control, the low-temperature concentration detection voltage VL1 is detected in the low-temperature measurement period TW; the high-temperature concentration detection voltage VH1 is detected in the high-temperature measurement period TW; and the temperature detection voltage VT is detected in the low- or high-temperature measurement period TW. It is feasible to obtain the detection voltage VL1, VH1, VT by taking one reading of the voltage VL1, VH1, VT in the time period TW, or by taking a plurality of readings of the voltage VL1, VH1, VT in the time period TW and by calculating a local average value of these readings. The detected voltages VL1, VH1 and VT are stored in the storage unit.

Subsequently, the gas concentration value X1 is determined from either the low-temperature concentration detection voltage VL1 or the high-temperature concentration detection voltage VH1 with reference to the concentration conversion data. The ambient temperature T is determined from the temperature detection voltage VT with reference to the temperature conversion data. The humidity H is also determined from the low-temperature concentration detection voltage VL1, the high-temperature concentration detection voltage VH1 and the temperature detection voltage VT with reference to the humidity conversion data. Further, the determined gas concentration value X1 is corrected by the ambient temperature T and the humidity H, and then, stored in the concentration storage area of the storage unit. (The storage unit is adapted to, if there is no empty space in the concentration storage area, overwrites from the oldest data).

At step S140, the microcomputer 7 checks whether a predetermined switching time T2 has elapsed. In the first embodiment, the switching time T2 is given as the sum of a judgment time $\Delta T$ and a judgment test initiation time T1 ($T2=T1+\Delta T$). The test initiation time T1 is determined as a time at which the first heating resistor 341 has not been deteriorated to a degree that makes it impossible to achieve required gas concentration measurement accuracy and, for example, can be set to the order of 1 day to several hundreds days. The judgment time $\Delta T$ is determined in such a manner as to minimize the possibility that the combustible gas concentration of the gas under measurement varies during a period of $2\times\Delta T$ and, for example, can be set to the order of several seconds.

If Yes at step S140 (it is judged that the time T2 has elapsed), the process goes to step S150.

If No at step S140, the process goes back to step S130 so that the microcomputer 7 repeats the calculation, output and storage of the gas concentration value X1. It means that the process operation of step S130 is repeated to calculate the gas concentration value X1 repeatedly in cycles of time $2\times TW$ (required for both of the low- and high-temperature measurement periods). As the number of times the calculation of the gas concentration value X1 is done during the judgment time $\Delta T$ is $\Delta T/(2\times TW)$, it is preferable to secure the space of the concentration storage area that is sufficient to store $\Delta T/(2\times TW)$ calculation results of the gas concentration value X1.

At step S150, the microcomputer 7 determines an average $X1_{\Delta T}$ of the calculation results of the gas concentration value X1 obtained over the time period $\Delta T$ from T1 to T2 and stored in the concentration storage area of the storage unit.

At step S160, the microcomputer 7 interrupts the energization signal S1 to the first energization control unit 50 so as to stop the energization of the bridge circuit 51 (the first heating resistor 341) of the first energization control unit 50 and outputs the energization signal S2 to the second energization control unit 60 so as to start energization of the bridge circuit 51 (the second heating resistor 342) of the second energization control unit 60.

At step S170, the microcomputer 7 calculates the gas concentration value X2 from the detection voltages VL2, VH2 and VT, stores the calculated gas concentration value X2 in the storage unit and outputs the calculated gas concentration value X2 to the external device.

In step S170, the calculation of the gas concentration value X2 is done in the same manner as in step S130. More specifically, the resistance of the bridge circuit 51 is switched under the switching signal CG2 from the microcomputer 7 so as to maintain the setting temperature of the second heating resistor 342 at the second setting temperature CL in a low-temperature measurement period TW", and then, maintain the setting temperature of the second heating resistor 342 at the first setting temperature CH in a high-temperature measurement period TW. In parallel to such temperature control, the low-temperature concentration detection voltage VL2 is detected in the low-temperature measurement period TW; the high-temperature concentration detection voltage VH2 is detected in the high-temperature measurement period TW; and the temperature detection voltage VT is detected in the low- or high-temperature measurement period TW. It is feasible to obtain the detection voltage VL2, VH2, VT by taking one reading of the voltage VL2, VH2, VT in the time period TW, or by taking a plurality of readings of the voltage VL2, VH2, VT in the time period TW and by calculating a local average value of these readings. Subsequently, the gas concentration value X2 is determined from the concentration detection voltage VL2 or VH2 with reference to the concentration conversion data. The ambient temperature T is determined from the temperature detection voltage VT with reference to the temperature conversion data. The humidity H is also determined from the detection voltages VL2, VH2 and VT with reference to the humidity conversion data. The determined gas concentration value X2 is corrected by the ambient temperature T and the humidity H, and then, stored in the concentration storage area of the storage unit.

At step S180, the microcomputer 7 checks whether a predetermined judgment test end time T3 has elapsed. The test end time T3 is given as the sum of the judgment time ΔT and the time T2 (T3=T2+ΔT) in the first embodiment.

If Yes at step S180 (it is judged that the time T3 has elapsed), the process goes to step S190.

If No at step S180, the process goes back to step S170 so that the microcomputer 7 repeats the calculation, output and storage of the gas concentration value X2. It means that the process operation of step S170 is also repeated to calculate the gas concentration value X2 repeatedly in cycles of time 2×TW (required for both of the low- and high-temperature measurement periods).

At step S190, the microcomputer 7 determines an average $X2_{\Delta T}$ of the calculation results of the gas concentration value X2 obtained over the time period ΔT from T2 to T3 and stored in the concentration storage area of the storage unit.

At step S200, the microcomputer 7 determines a difference Y between the average gas concentration value $X1_{\Delta T}$ obtained in step S150 and the average gas concentration value $X2_{\Delta T}$ obtained in step S190 ($Y=X1_{\Delta T}-X2_{\Delta T}$).

At step S210, the microcomputer 7 interrupts the energization signal S2 so as to stop the energization of the bridge circuit 51 (the second heating resistor 342) of the second energization control unit 60.

At step S220, the microcomputer 7 checks whether the absolute value |Y| of the concentration difference obtained in step S200 is smaller than or equal to a given threshold value THy. The threshold value THy is set as appropriate depending on the gas concentration measurement accuracy required for various processing operations using the gas concentration detection value X1 and can be set to e.g. 0.4% $H_2$.

If Yes at step S220, the process goes back to step S110 upon judging that no anomaly is occurring in the first heating resistor 341 so that the microcomputer 7 conducts the above process operations of steps S110 to S210 repeatedly.

If No at step S220, the process goes to step S230 upon judging that the anomaly is occurring in the first heating resistor 341.

At step S230, the microcomputer 7 generates and outputs an anomaly detection signal to the external device so as to inform the occurrence of the anomaly in the first heating resistor 341.

At step S240, the microcomputer 7 turns off the actuation switch 9 and thereby stops the combustible gas detection apparatus 1. The process exits.

In the first embodiment, steps S140, S160, S180 and S210 corresponds to a normal-state operation section; and step S240 corresponds to a first abnormal-state operation section.

Figure 5A:
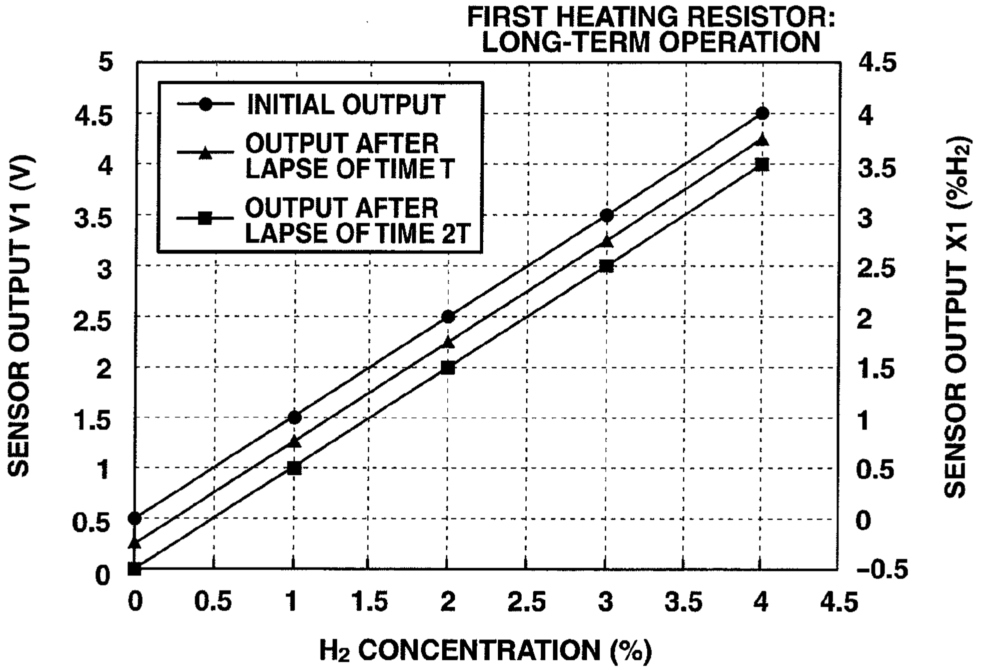
FIG. 5A and FIG. 5B are graphs showing changes with time of the output characteristics of first and second heating resistors of the gas sensor, respectively, in the combustible gas detection apparatus according to the first embodiment of the present invention.
Figure 5B:
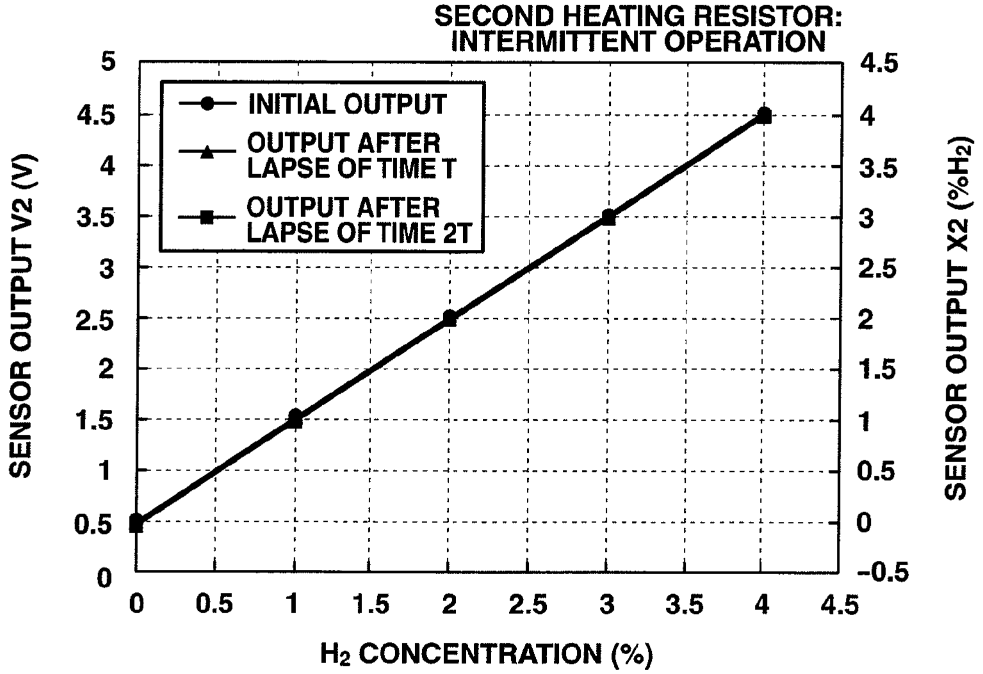
Figure 6:
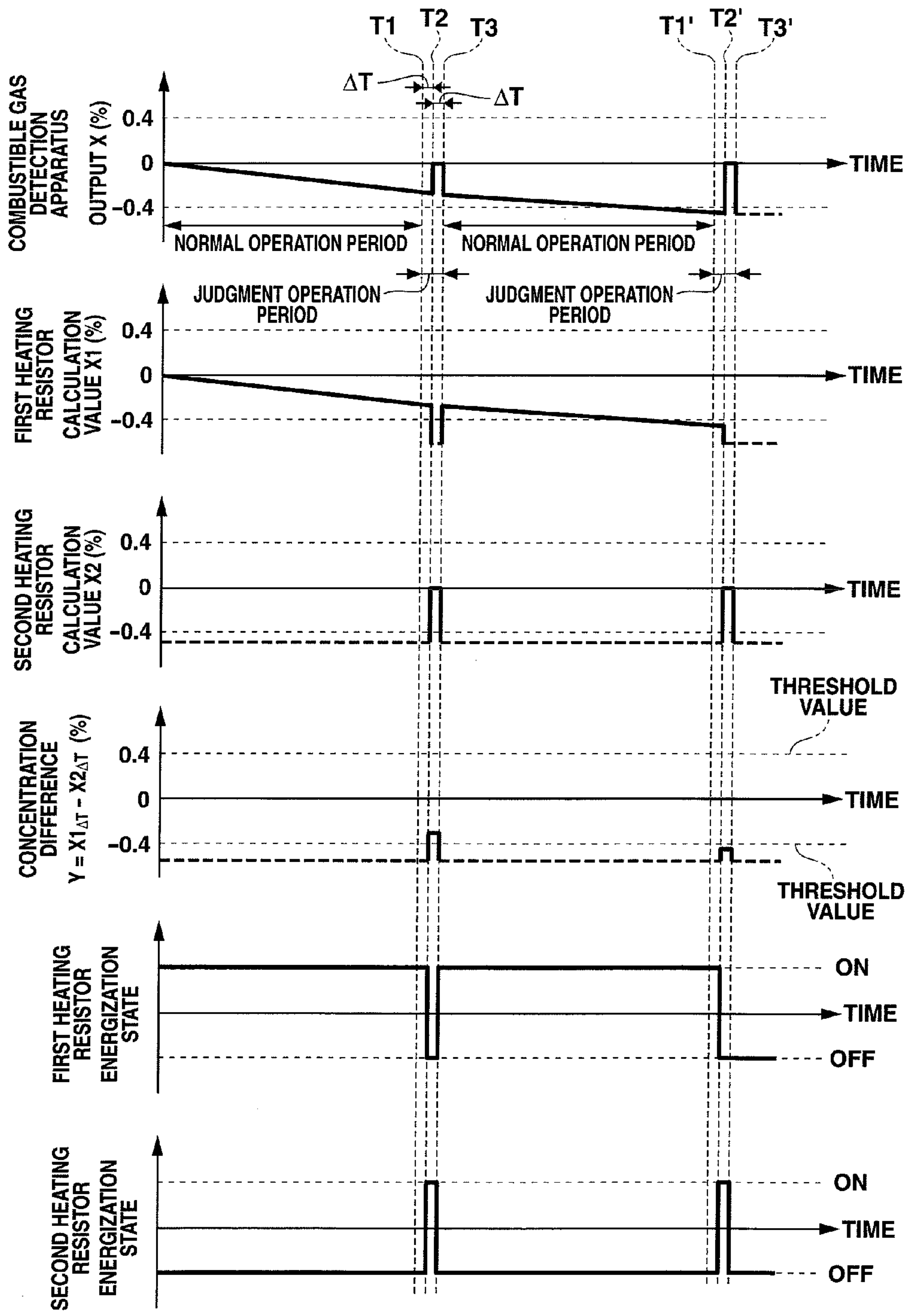
FIG. 6 is a time chart showing process operations of the combustible gas detection apparatus according to the first embodiment of the present invention.

It is herein assumed that the output characteristics of the first and second heating resistors 341 and 342 are measured at time 0, time T1 and time 2×T1 in the case of operating the first heating resistor 341 continuously over a long time while operating the second heating resistor 342 intermittently for the judgment time ΔT. The measurement results are shown in FIGS. 5A and 5B. In FIGS. 5A and 5B, time T1 is set to 400 days. As shown in FIG. 5A, the output characteristics of the first heating resistor 341 change with time. Although the output characteristics of the first heating resistor 341 increase with time in FIG. 5A, there may be a case that the output characteristics of the first heating resistor 341 decrease with time as shown in FIG. 6. Due to such changes in the output characteristics of the first heating resistor 341, the accuracy of the detection signal V1, and by extension, the calculation accuracy of the gas concentration value X1 become deteriorated with the passage of time. On the other hand, there is almost no difference in the output characteristics of the second heating resistance 342 as shown in FIG. 5B. The output characteristics of the second heating resistor 342 can be maintained over a long time.

Under the above gas concentration measurement process, the combustible gas detection apparatus 1 alternately repeats normal operation periods (e.g. periods from time 0 to time T1 and from time T3 to time T1') and judgment operation periods (e.g. periods from time T1 to time T3 and from time T1' to time T3') as shown in FIG. 6. In FIG. 6, time T1 is set to 400 days as in FIGS. 5A and 5B.

At time 0, the combustible gas detection apparatus 1 becomes actuated in the normal operation mode so that the microcomputer 7 controls the first energization control unit 50 to start energization of the first heating resistor 341 and calculates the gas concentration value X1 based on the detection signal V1 of the first heating resistor 341.

At time T1, the combustible gas detection apparatus 1 shifts to the judgment operation mode while the microcomputer 7 controls the first energization control unit 50 to continue the energization of the first heating resistor 341 and repeatedly calculates the gas concentration value X1 based on the detection signal V1 of the first heating resistor 341. The calculation results of the gas concentration value X1 are stored and accumulated in the concentration storage area of the microcomputer 7 over the time period ΔT from T1 to T2.

At time T2, the microcomputer 7 determines the average $X1_{\Delta T}$ of the accumulated calculation results of the gas concentration value X1. At the same time, the microcomputer 7 controls the first energization section 50 to stop the energization of the first heating resistor 341 and controls the second energization control section 60 to start the energization of the second heating resistor 342 and repeatedly calculates the gas concentration value X2 based on the detection signal V2 of the second heating resistor 342. The calculation results of the gas concentration value X2 are stored and accumulated (as a reference for judgment) in the concentration storage area of the microcomputer 7 over the time period ΔT from T2 to T3.

At time T3, the microcomputer 7 determines the average $X2_{\Delta T}$ of the accumulated calculation results of the gas concentration value X2 and controls the second energization control unit 60 to stop the energization of the second heating resistor 342.

The microcomputer 7 further determines the difference Y between the average gas concentration values $X1_{\Delta T}$ and $X2_{\Delta T}$ and compares the absolute value |Y| of the concentration difference with the threshold value THy. At this point (time T3), the absolute value |Y| is smaller than the threshold value THy. The microcomputer 7 thus judges that no anomaly is occurring in the first heating resistor 341.

Then, the combustible gas detection apparatus 1 shifts to the normal operation mode so that the microcomputer 7 controls the first energization control unit 50 to restart the energization of the first heating resistor 341 and calculates the gas concentration value X1 based on the detection signal V1 of the first heating resistor 341.

At time T1', the combustible gas detection apparatus 1 shifts to the judgment operation mode. During the period from time T1' to T3, the microcomputer 7 conducts the same process operations as those from time T1 to T3.

At time T3', the absolute value |Y| exceeds the threshold value THy. Upon judging that the anomaly is occurring in the first heating resistor 341, the microcomputer 7 controls the first and second energization control units 50 and 60 to stop the energization of the first and second heating resistors 341 and 342 whereby the combustible gas detection apparatus 1 comes to a stop.

In this way, the combustible gas detection apparatus 1 of the first embodiment is configured to alternately energize the first and second heating resistors 341 and 342 in the judgment operation period so as to de-energize the second heating resistor 342 during the energization of the first heating resistor 341 and to de-energize the first heating resistor 341 during the energization of the second heating resistor 342. It is therefore possible in the combustible gas detection apparatus 1 to not only calculate the gas concentration value X1, X2 based on the detection signal V1, V2 of either one of the heating resistors 341 and 342, without the influence of heat generated by the other heating resistor 341, 342, and detect the anomaly in the first heating resistor 341 accurately by comparison of these calculation values X1 and X2.

Further, the combustible gas detection apparatus 1 of the first embodiment is configured to energize only the first heating resistor 341 in the normal operation period so as to calculate the gas concentration value X1 based on the detection signal V1 of the first heating resistor 341 as the combustible gas concentration X, and energize each of the first and second heating resistors 342 for the judgment time $\Delta T$ in the judgment operation period so as to calculate the gas concentration values X1 and X2 based on the detection signals V1 and V2 of the first and second heating resistors 341 and 342 and judge the occurrence or non-occurrence of the anomaly in the first heating resistor 341. As the frequency of use of the second heating resistor 342 is made lower than that of the first heating resistor 341, it is possible to prevent deterioration of the second heating resistor 342 used as a reference for judgment and detect the anomaly in the first heating resistor 341 accurately over a long time.

Second Embodiment

Figure 7:
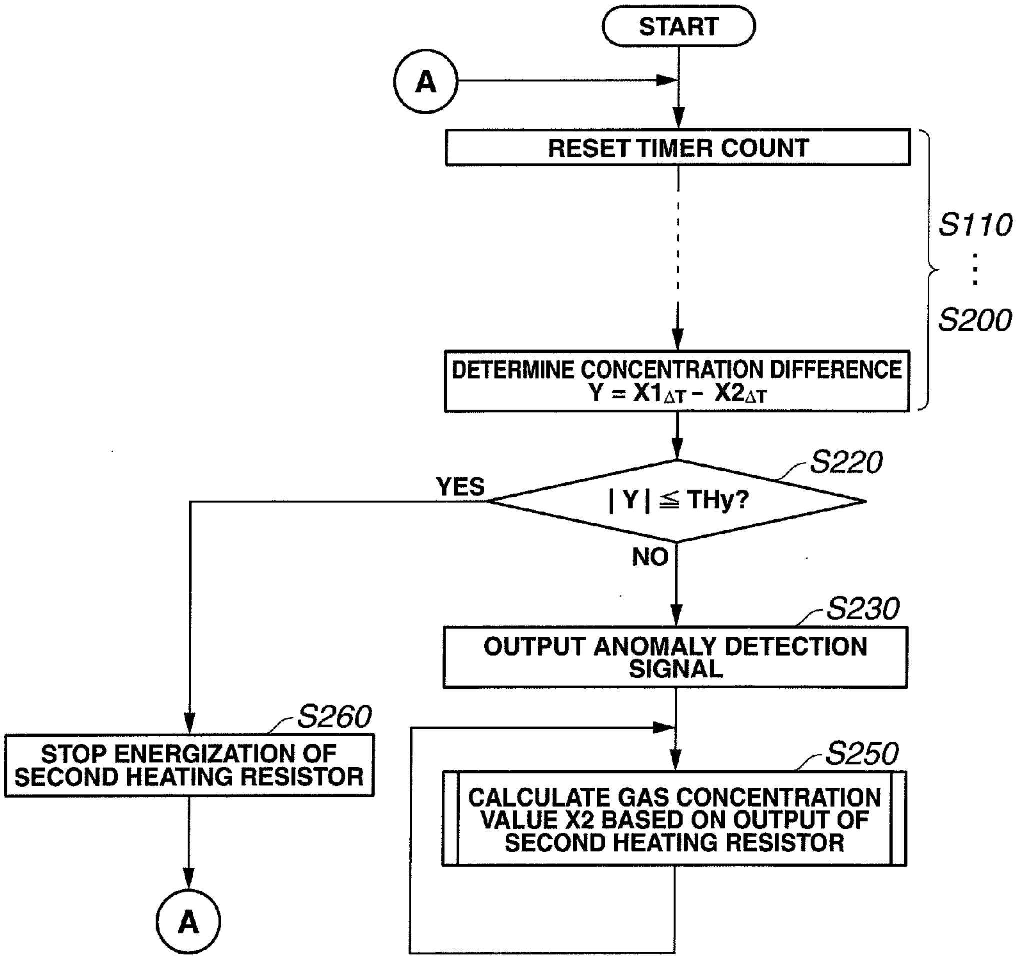
FIG. 7 is a flowchart of gas concentration measurement process of a combustible gas detection apparatus according to a second embodiment of the present invention.

The second embodiment is similar to the first embodiment, except for a part of the gas concentration measurement process executed by the microcomputer 7 as shown in FIG. 7. Herein, the process operations of steps S110 to S200 of FIG. 7 in the second embodiment are the same as those of FIG. 3 in the first embodiment; and detailed explanations of these process operations of S110 to S200 will be thus omitted.

Upon determination of the concentration difference Y at S200, the microcomputer 7 checks, at step S220, whether the absolute value |Y| of the concentration difference obtained in step S200 is smaller than or equal to a given threshold value THy to thereby judge the occurrence of an anomaly in the first heating resistor 341 without stopping the energization of the second heating resistor 342.

If Yes at step S220, the process goes to step S260 upon judging that no anomaly is occurring in the first heating resistor 341.

If No at step S220, the process goes to step S230 upon judging that the anomaly is occurring in the first heating resistor 341.

At step S230, the microcomputer 7 generates and outputs an anomaly detection signal to the external device so as to inform the occurrence of the anomaly in the first heating resistor 341. The process then goes to step S250.

At step S250, the microcomputer 7 repeatedly calculates the gas concentration value X2 based on the output of the second heating resistor 342 (in the same manner as in step S170) to thereby continue the gas concentration detection operations.

At step S260, the microcomputer 7 interrupts the energization signal S2 so as to stop the energization of the bridge circuit 51 (the second heating resistor 342) of the second energization control unit 60. The process then goes back to step S110.

In the second embodiment, step 250 corresponds to a second abnormal-state operation section.

It is therefore possible in the second embodiment that, even in the event of the anomaly in the first heating resistor 341, the combustible gas detection apparatus 1 can continue the gas concentration detection operations by means of the second heating resistor 342 in which almost no deterioration has occurred although the gas concentration detection operations are terminated upon detection of the occurrence of the anomaly in the first heating resistor 341 in the first embodiment.

Third Embodiment

Figure 8:
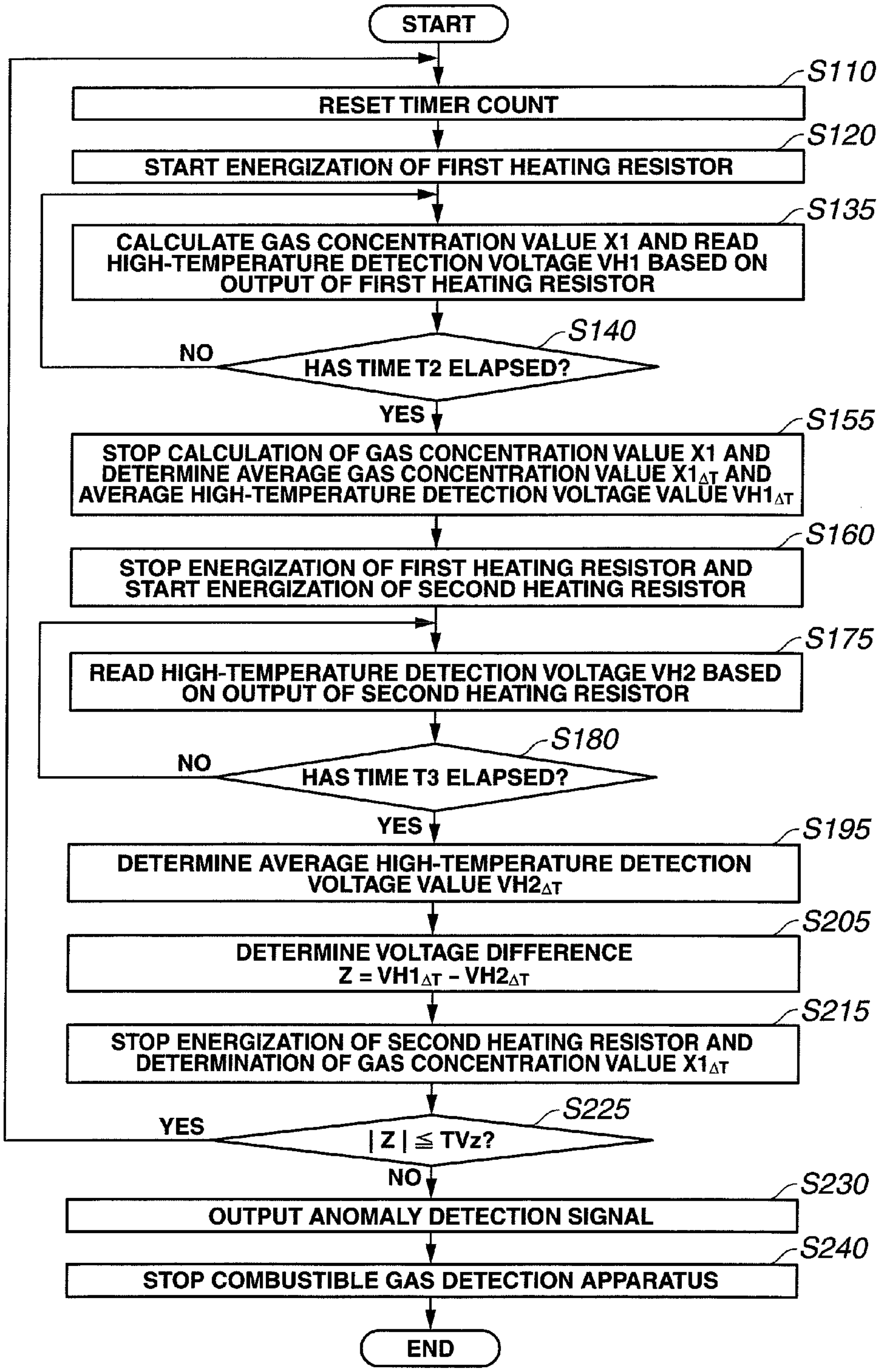
FIG. 8 is a flowchart of gas concentration measurement process of a combustible gas detection apparatus according to a third embodiment of the present invention.

The third embodiment is similar to the first embodiment, except for a part of the gas concentration measurement process executed by the microcomputer 7 as shown in FIG. 8. In the third embodiment, the gas concentration measurement process includes process operations of steps S135, S155, S175, S195, S205, S215 and S225 in place of the process operations of steps S130, S150, S170, S190, S200, S210 and S220 of FIG. 3, respectively. The following explanations will be thus focused on these process operations of steps S135, S155, S175, S195, S205, S215 and S225. Herein, the microcomputer 7 has a concentration storage area to store therein the calculation results of the gas concentration value X1 and a high-temperature concentration detection voltage storage area to store therein the detection results of the high-temperature concentration detection voltages VH1, VH2.

At step S135, the microcomputer 7 calculates the gas concentration value X1 from the detection voltages VL1, VH1 and VT, stores the calculated gas concentration value X1 in the concentration storage area of the storage unit and outputs the calculated gas concentration value X1 to the external device. At this time, the microcomputer 7 also stores, in the high-temperature voltage storage area of the storage unit, the high-temperature concentration detection voltage VH1 used for calculation of the gas concentration value X1.

At step S155, the microcomputer 7 determines an average $X1_{\Delta T}$ of the calculation results of the gas concentration value X1 obtained over the time period $\Delta T$ from T1 to T2 and stored in the concentration storage area of the storage unit and determines an average $VH1_{\Delta T}$ of the detection results of the high-temperature concentration detection voltage VH1 obtained over the time period $\Delta T$ from T1 to T2 and stored in the high-temperature concentration detection voltage storage area of the storage unit. Then, the microcomputer 7 outputs the average gas concentration value $X1_{\Delta T}$, in place of the gas concentration value X1 outputted in step S135, to the external device.

At step S175, the microcomputer 7 detects the high-temperature gas concentration detection voltage VH2 from the second heating resistor 342 and stores the detected high-temperature concentration detection voltage VH2 in the high-temperature concentration detection voltage storage area of the storage unit.

At step S195, the microcomputer 7 determines an average $VH2_{\Delta T}$ of the detection results of the high-temperature concentration detection voltage VH2 obtained over the time period $\Delta T$ from T2 to T3 and stored in the high-temperature voltage storage area of the storage unit.

At step S205, the microcomputer 7 determines a difference Z between the average high-temperature voltage $VH1_{\Delta T}$ obtained in step S155 and the average high-temperature voltage $VH2_{\Delta T}$ obtained in step S195 ($Z=VH1_{\Delta T}-VH2_{\Delta T}$).

At step S215, the microcomputer 7 interrupts the energization signal S2 so as to stop the energization of the bridge circuit 51 (the second heating resistor 342) of the second energization control unit 60. The microcomputer 7 also stops the output of the average gas concentration value $X1_{\Delta T}$ to the external device.

At step S225, the microcomputer 7 checks whether the absolute value $|Z|$ of the voltage difference obtained in step S205 is smaller than or equal to a given threshold value TVz. The threshold value TVy is set as appropriate depending on the gas concentration detection accuracy required for various processing operations in which the gas concentration detection value X1 is utilized and can be set to e.g. 15 mV.

If Yes at step S225 ($|Z|\leq TVz$), the process goes back to step S110 upon judging that no anomaly is occurring in the first heating resistor 341.

If No at step S225 ($|Z|>TVz$), the process goes to step S230 upon judging that an anomaly is occurring in the first heating resistor 341.

Figure 9:
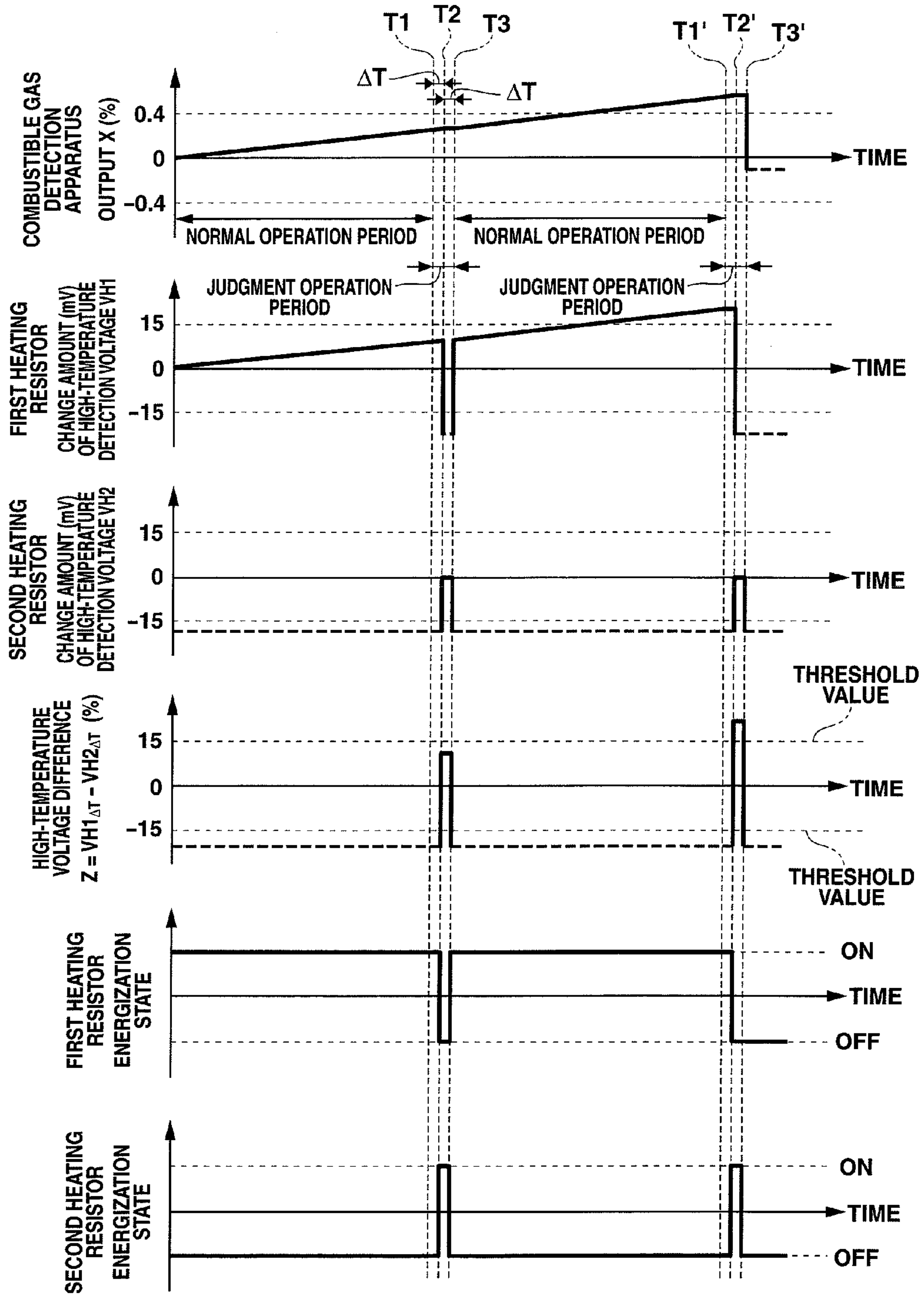
FIG. 9 is a time chart showing process operations of the combustible gas detection apparatus according to the third embodiment of the present invention.

Under the above gas concentration measurement process, the combustible gas detection apparatus 1 alternately repeats normal operation periods (e.g. periods from time 0 to time T1 and from time T3 to time T1') and judgment operation periods (e.g. periods from time T1 to time T3 and from time T3 to time T1') as shown in FIG. 9.

As the output characteristics of the first heating resistor 341 change with time during continuous long-term use in the normal operation periods, the accuracy of the high-temperature concentration detection voltage VH1, and by extension, the calculation accuracy of the gas concentration value X1 become deteriorated with the passage of time due to such changes in the output characteristics of the first heating resistor 341.

At time T2 (the lapse of time T2 from the start of energization of the first heating resistor 341), the microcomputer 7 determines the average $X1_{\Delta T}$ of the calculation results of the gas concentration value X1 stored and accumulated in the concentration storage area over the time period $\Delta T$ from T1 to T2, and then, output the average gas concentration value $X1_{\Delta T}$ in place of the gas concentration value X1. The microcomputer 7 also determines the average $VH1_{\Delta T}$ of the detection results of the high-temperature concentration detection voltage VH1 stored and accumulated in the concentration storage area over the time period $\Delta T$ from T1 to T2. Further, the microcomputer 7 controls the first energization control unit 50 to stop the energization of the first heating resistor 341, controls the second energization control unit 60 to start energization of the second heating resistor 342 the microcomputer 7 and detects the high-temperature gas concentration detection voltage VH2 from the second heating resistor 342.

At time T3, the microcomputer 7 determines the average $VH2_{\Delta T}$ of the detection results of the high-temperature concentration detection voltage VH2 stored and accumulated in the concentration storage area over the time period $\Delta T$ from T2 to T3 and controls the second energization control unit 60 to stop the energization of the second heating resistor 342.

The microcomputer 7 further determines the difference Z between the average gas concentration values $VH1_{\Delta T}$ and $VH2_{\Delta T}$ and compares the absolute value $|Z|$ of the voltage difference with the threshold value THz. At this point (time T3), the absolute value $|Z|$ is smaller than the threshold value THz. The microcomputer 7 thus judges that no anomaly is occurring in the first heating resistor 341.

Then, the microcomputer 7 controls the first energization control unit 50 to restart the energization of the first heating resistor 341 and calculates the gas concentration value X1 continuously up until time T2'.

From time T2', the microcomputer 7 conducts the same process operations as those from time T2.

At time T3', the absolute value $|Z|$ exceeds the threshold value THz. Upon judging that the anomaly is occurring in the first heating resistor 341, the microcomputer 7 controls the first and second energization control units 50 and 60 to stop the energization of the first and second heating resistors 341 and 342 whereby the combustible gas detection apparatus 1 comes to a stop.

The combustible gas detection apparatus 1 of the third embodiment is configured to judge the occurrence of the anomaly in the first heating resistor 341 by comparison of the average values $VH1_{\Delta T}$ and $VH2_{\Delta T}$ of the high-temperature concentration detection voltages V1 and V2 used for calculation of the average gas concentration values $X1_{\Delta T}$ and $X2_{\Delta T}$, rather than by comparison of the average gas concentration values $X1_{\Delta T}$ and $X2_{\Delta T}$. It is therefore possible in the third embodiment to not only obtain the same effects as in the first embodiment, but also significantly reduce the amount of data processing for judgment of the occurrence of the anomaly in the first heating resistor 341 without the need to calculate the gas concentration value X2 from the detection signal V2 of the second heating resistor 342.

The combustible gas detection apparatus 1 of the third embodiment is further configured to, during the time period $\Delta T$ from T2 to T3 where the energization control of the second heating resistor 342 is performed, output the average $X1_{\Delta T}$ of the calculation results of the gas concentration value X1 obtained over the immediately preceding time period from T1 to T2, in place of the real-time calculation result of the gas concentration value X1, to the external device. It is thus possible for the combustible gas detection apparatus 1 to continuously output the gas concentration detection result X to the external device even during the energization of the second heating resistor 342.

Fourth Embodiment

Figure 10:
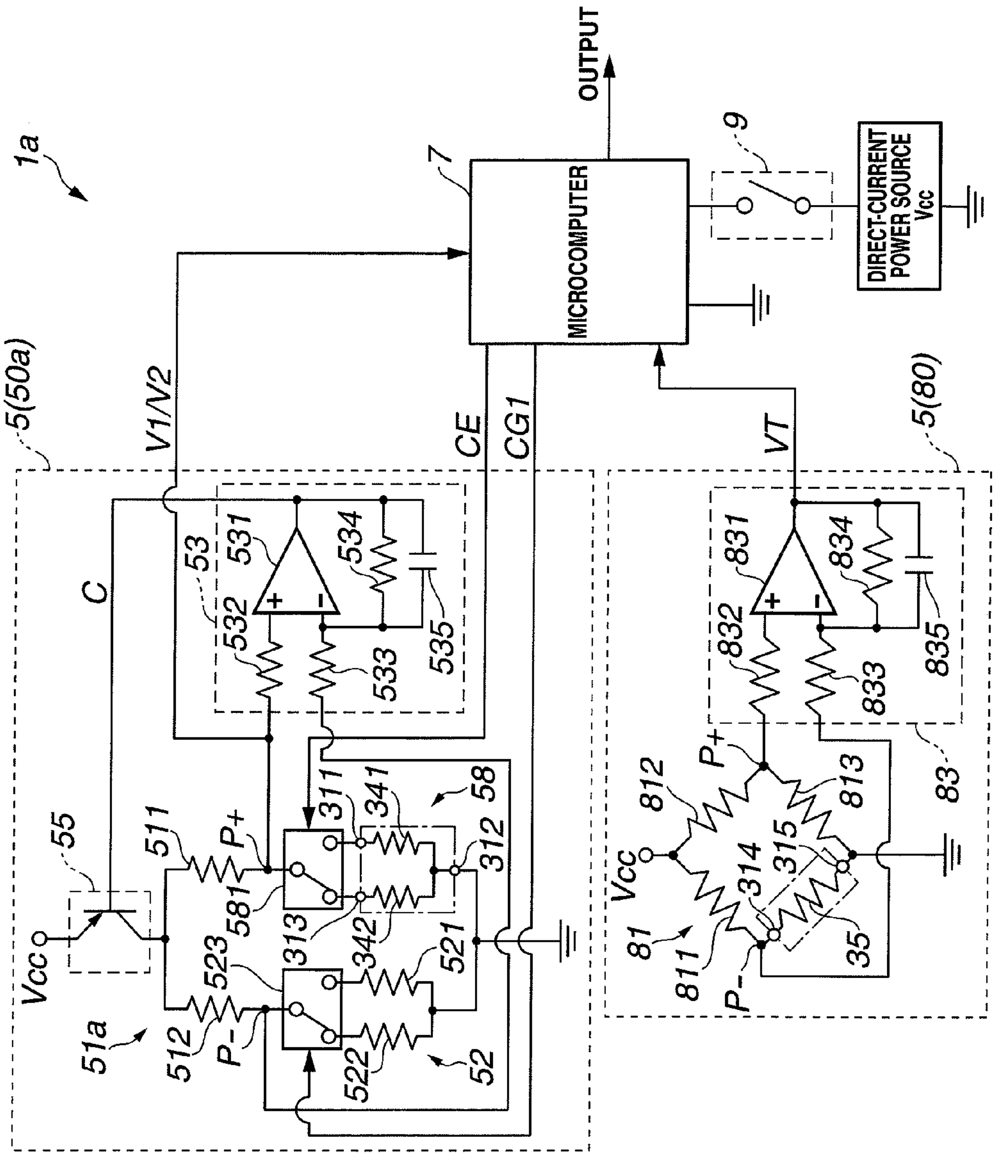
FIG. 10 is a block diagram of a combustible gas detection apparatus according to a fourth embodiment of the present invention.

The forth embodiment specifically refers to a combustible gas detection apparatus 1*a* as shown in FIG. 10, which includes a gas sensor 3 placed in and exposed to a gas under measurement to measure a combustible gas concentration of the gas under measurement, a drive control circuit assembly 5 for performing drive control of the gas sensor 3, a microcomputer 7 for generating various control signals such as switching signals CG and CE to control operations of the drive control circuit assembly 5 and performing various operation processes including gas concentration measurement process based on output signals V1, V2 and VT from the drive control circuit assembly 5, and an actuation switch 9 for connecting or disconnecting a power supply line from a direct-current power source Vcc to the microcomputer 7 and thereby actuating or stopping the microcomputer 7.

The combustible gas detection apparatus 1*a* of the fourth embodiment is similar to the combustible gas detection apparatus 1 of the first embodiment, except for the configuration of a part of the drive control circuit assembly 5, except for a part of signal data transmitted between the drive control circuit assembly 5 and the microcomputer 7 and thereby except for a part of the gas concentration measurement process executed by the microcomputer 7.

In the fourth embodiment, the drive control circuit assembly 5 includes an energization control unit 50*a* to select either one of the first and second heating resistors 341 and 342 as an energization control target, perform energization control of the selected heating resistor 341, 342 and output a voltage across the heating resistor 341, 342 as the detection signal V1, V2 responsive to the combustible gas concentration of the gas under measurement and a temperature measurement unit 80 to perform energization control of the temperature-measuring resistor 35 and output the detection signal VT responsive to the temperature of the gas under measurement.

The temperature measurement unit 80 of the fourth embodiment is similar in configuration to that of the first embodiment.

The energization control unit 50*a* of the fourth embodiment is similar but different in configuration from the first energization control unit 50 of the first embodiment, in that the energization control unit 50*a* has no switching circuit 57 and has a bridge circuit 51*a* with a resistor switching block 58 to switch the energization control target between the first and second heating resistors 341 and 342 in place of the bridge circuit 51. As shown in FIG. 10, the resistor switching block 58 has a switching element 581 that switches the connection between the first and second heating resistors 341 and 342 to alternately select and operate either one of the first and second heating resistors 341 and 342 as a bridge circuit component according to the switching signal CE from the microcomputer 7. Further, a junction P+ of the fixed resistor 511 and the switching element 581 is connected to the non-inverting input terminal of the operational amplifier 531 via the fixed resistor 532; and a junction P− of the fixed resistor 512 and the variable resistance element 52 is connected to the inverting input terminal of the operational amplifier 531 via the fixed resistor 533. In this configuration, the bridge circuit 51*a* is adapted to output the potential at the junction P+, i.e., the voltage across the first heating resistor 341 as the detection signal V1 when the switching signal SE is to select the first heating resistor 341 and the voltage across the second heating resistor 342 as the detection signal V2 when the switching signal SE is to select the second heating resistor 342. In the fourth embodiment, the energization control unit 50*a* serves as a selector and as a third energization controller.

Upon power supply from the direct-current power source Vcc, the amplifier circuit 53 and the current regulator circuit 55 are operated to regulate the flow of current through the bridge circuit 51*a* in such a manner that the potential difference between the junctions P+ and P− becomes zero. Under such current regulation control, the resistance of either one of the first and second heating resistors 341 and 342 selected by the switching element 581 according to the switching signal CE is adjusted to a given constant level depending on the resistance value of the fixed resistor 521 or 522 selected by the selector switch 523 of the variable resistance element 52 according to the switching signal CG1. The temperature of the selected one of the first and second heating resistors 341 and 342 is thus controlled to the first setting temperature CH or the second setting temperature CL. When the switching element 581 is connected to the first heating resistor 341 according to the switching signal CE, the bridge circuit 51*a* outputs as the detection signal V1 the high-temperature concentration detection voltage VH1 in the high-temperature measurement period by selection of the fixed resistor 521 according to the switching signal CG and outputs the low-temperature concentration detection voltage VL1 in the low-temperature measurement period as the detection signal V1 by selection of the fixed resistor 522 according to the switching signal CG. When the switching element 581 is connected to the second heating resistor 342 according to the switching signal CE, the bridge circuit 51*a* outputs as the detection signal V2 the high-temperature concentration detection voltage VH2 in the high-temperature measurement period by selection of the fixed resistor 521 according to the switching signal CG and outputs the low-temperature concentration detection voltage VL2 in the low-temperature measurement period as the detection signal V2 by selection of the fixed resistor 522 according to the switching signal CG. In this way, the drive control circuit assembly 5 of the fourth embodiment uses different control signals but generates the same detection signals V1 and V2 as those of the first embodiment. It is herein noted that the reason for the placement of no switching circuit 57 in the energization control unit 50*a* is that the energization control unit 50*a* allows energization of the bridge circuit 51*a* at all times for energization control of both of the first and second heating resistors 341 and 342.

The gas concentration measurement process executed by the microcomputer 7 of the fourth embodiment is the same as that of the first embodiment, except for using the switching signal CE in place of the energization signals S1 and S2 at the time of switching the energization control target between the heating resistors 341 and 342 and except for using the switching signal CG at the time of switching the setting temperature of each of the heating resistors 341 and 342 under energization control.

As mentioned above, the combustible gas detection apparatus 1*a* of the fourth embodiment is provided with a single energization control unit 50*a* to alternately select the first and second heating resistors 341 and 342 as the energization control target and perform energization control of the selected one of the first and second heating resistors 341 and 342 although the combustible gas detection apparatus 1 of the first embodiment is provided with two separate energization control units 50 and 60 for alternate energization control of the first and second heating resistors 341 and 342. It is therefore possible in the fourth embodiment to significantly simplify the structure of the combustible gas detection apparatus 1*a* so that the combustible gas detection apparatus 1*a* can be reduced in size and cost.

The entire contents of Japanese Patent Application No. 2010-093976 (filed on Apr. 15, 2010) and No. 2011-036033 (filed on Feb. 22, 2011) are herein incorporated by reference.

Although the present invention has been described with reference to the above first to fourth embodiments, the present invention is not limited to these specific exemplary embodiments. Various modifications and variations of the embodiments described above will occur to those skilled in the art in light of the above teachings.

For example, the first and second heating resistors 341 and 342 may be mounted on different substrates although the first and second heating resistors 341 and 342 are mounted on the same substrate in the above embodiments. Further, the number of the heating resistors 34 is not limited to two. The gas sensor 3 may have three or more heating resistors 34. In this case, the combustible gas detection apparatus 1, 1*a* is configured to perform energization control of the heating resistors 34 so as not to simultaneously energize two or more of the heating resistors 34.

In the above embodiments, the variable resistance element 52 is used in each of the energization control units 50, 60 and 50*a* so as to switch the setting temperature of the heating resistor 34 between the first and second setting temperatures CH and CL. Alternatively, the energization control unit 50, 60, 50*a* may use a fixed resistor in place of the variable resistance element 52 in the case where there are only small changes in the humidity of the gas under measurement.

Although the combustible gas detection apparatus 1, 1*a* is configured to judge the occurrence of the anomaly in the first heating resistor 341 at regular intervals (every time T) in the above embodiments, it is alternatively feasible to judge the occurrence of the anomaly in the first heating resistor 341 every time equipment in which the combustible gas detection apparatus 1, 1*a* is installed becomes actuated, or in the case where the possibility of change of the combustible gas concentration is low according to the operating conditions of the equipment in which the combustible gas detection apparatus 1, 1*a* is installed.

The scope of the invention is defined with reference to the following claims.

What is claimed is:

1. A combustible gas detection apparatus for measuring a combustible gas concentration of a gas under measurement, comprising:

a combustible gas sensor having first and second heating resistors, each of which being placed in the gas under measurement and having a resistance that changes depending on the combustible gas concentration of the gas under measurement; and a control device having:

an energization control section that alternately energizes the first and second heating resistors in such a manner as to adjust the resistance of each of the first and second heating resistors to a given value corresponding to a predetermined setting temperature;

a first calculation section that calculates a first calculation value responsive to the combustible gas concentration of the gas under measurement based on a voltage across the first heating resistor during energization of the first heating resistor;

a second calculation section that calculates a second calculation value responsive to the combustible gas concentration of the gas under measurement based on a voltage across the second heating resistor during energization of the second heating resistor; and an anomaly judgment section that judges the occurrence or non-occurrence of an anomaly in the first heating resistor by comparison of the first and second calculation values, wherein the anomaly judgment section is actuated every time a predetermined judgment condition is satisfied, wherein the control device has a normal-state operation section that, upon satisfaction of the predetermined judgment condition, causes the energization control section to allow the energization of the second heating resistor only for a time period required to measure the voltage across the second heating resistor for calculation of the second calculation value and to allow the energization of the first heating resistor at all times other than said time period, wherein the energization control section de-energizes the first heating resistor during the energization of the second heating resistor and de-energizes the second heating resistor during the energization of the first heating resistor, and wherein the control device has an abnormal-state operation section that, when the anomaly judgment section judges that the anomaly is occurring in the first heating resistor, controls the energization control section to stop the energization of the first and second heating resistors.

2. The combustible gas detection apparatus according to claim 1, wherein the first and second heating resistors are mounted on the same substrate.

3. The combustible gas detection apparatus according to claim 1, wherein the anomaly judgment section judges that the anomaly is occurring in the first heating resistor when either a difference between the first and second calculation values or a ratio between the first and second calculation value exceeds a given threshold value.

4. The combustible gas detection apparatus according to claim 1, wherein the first calculation section converts the voltage across the first heating resistor to a gas concentration value and gives the gas concentration value as the first calculation value; and wherein the second calculation section converts the voltage across the second heating resistor to a gas concentration value and gives the gas concentration value as the second calculation value.

5. The combustible gas detection apparatus according to claim 1, wherein the first calculation section calculates an average value of the voltage across the first heating resistor as the first calculation value; and wherein the second calculation section calculates an average value of the voltage across the second heating resistor as the second calculation value.

6. The combustible gas detection apparatus according to claim 1, wherein the energization control section has a first energization controller that controls the energization of the first heating resistor and a second energization controller that controls the energization of the second heating resistor and operates the first and second energization controllers alternately for alternate energization control of the first and second heating resistors.

7. The combustible gas detection apparatus according to claim 1, wherein the energization control section has a selector that selects one of the first and second heating resistors as a control target and an energization controller that controls the energization of the selected one of the first and second heating resistors.

8. A combustible gas detection apparatus for measuring a combustible gas concentration of a gas under measurement, comprising:

a combustible gas sensor having first and second heating resistors, each of which being placed in the gas under measurement and having a resistance that changes depending on the combustible gas concentration of the gas under measurement; and a control device having:

an energization control section that alternately energizes the first and second heating resistors in such a manner as to adjust the resistance of each of the first and second heating resistors to a given value corresponding to a predetermined setting temperature;

a first calculation section that calculates a first calculation value responsive to the combustible gas concentration of the gas under measurement based on a voltage across the first heating resistor during energization of the first heating resistor;

a second calculation section that calculates a second calculation value responsive to the combustible gas concentration of the gas under measurement based on a voltage across the second heating resistor during energization of the second heating resistor; and an anomaly judgment section that judges the occurrence or non-occurrence of an anomaly in the first heating resistor by comparison of the first and second calculation values, wherein the anomaly judgment section is actuated every time a predetermined judgment condition is satisfied, wherein the control device has a normal-state operation section that, upon satisfaction of the predetermined judgment condition, causes the energization control section to allow the energization of the second heating resistor only for a time period required to measure the voltage across the second heating resistor for calculation of the second calculation value and to allow the energization of the first heating resistor at all times other than said time period, wherein the energization control section de-energizes the first heating resistor during the energization of the second heating resistor and de-energizes the second heating resistor during the energization of the first heating resistor, and wherein the control device has an abnormal-state operation section that, when the anomaly judgment section judges that the anomaly is occurring in the first heating resistor, controls the energization control section to energize the second heating resistor and controls the second calculation section to calculate the second calculation value.

9. The combustible gas detection apparatus according to claim 8, wherein the first and second heating resistors are mounted on the same substrate.

10. The combustible gas detection apparatus according to claim 8, wherein the anomaly judgment section judges that the anomaly is occurring in the first heating resistor when either a difference between the first and second calculation values or a ratio between the first and second calculation value exceeds a given threshold value.

11. The combustible gas detection apparatus according to claim 8, wherein the first calculation section converts the voltage across the first heating resistor to a gas concentration value and gives the gas concentration value as the first calculation value; and wherein the second calculation section converts the voltage across the second heating resistor to a gas concentration value and gives the gas concentration value as the second calculation value.

12. The combustible gas detection apparatus according to claim 8, wherein the first calculation section calculates an average value of the voltage across the first heating resistor as the first calculation value; and wherein the second calculation section calculates an average value of the voltage across the second heating resistor as the second calculation value.

13. The combustible gas detection apparatus according to claim 8, wherein the energization control section has a first energization controller that controls the energization of the first heating resistor and a second energization controller that controls the energization of the second heating resistor and operates the first and second energization controllers alternately for alternate energization control of the first and second heating resistors.

14. The combustible gas detection apparatus according to claim 8, wherein the energization control section has a selector that selects one of the first and second heating resistors as a control target and an energization controller that controls the energization of the selected one of the first and second heating resistors.

* * * * *